US00PP23918P2

(12) United States Plant Patent
Sakaue

(10) Patent No.: US PP23,918 P2
(45) Date of Patent: Sep. 24, 2013

(54) ***CAMPSIS* PLANT NAMED 'TAKARAZUKA YELLOW'**

(50) Latin Name: *Campsis×tagliabuana*
Varietal Denomination: Takarazuka Yellow

(76) Inventor: Koichi Sakaue, Takarazuka (JP)

( * ) Notice: Subject to any disclaimer, the term of this patent is extended or adjusted under 35 U.S.C. 154(b) by 101 days.

(21) Appl. No.: 13/385,122

(22) Filed: Feb. 2, 2012

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Susan McCormick Ewoldt
(74) *Attorney, Agent, or Firm* — Penny J. Aguirre

(57) ABSTRACT

A new cultivar of *Campsis* hybrid, 'Takarazuka Yellow', characterized by its very dark green, clean foliage, its large flowers that are peach orange in color when they open and mature to yellow in color with throats that are orange-red with red veining, and its compact, upright and vining plant habit.

2 Drawing Sheets

Botanical classification: *Campsis×tagliabuana.*
Variety denomination: 'Takarazuka Yellow'.

CROSS REFERENCE TO RELATED APPLICATIONS

This application is co-pending with U.S. Plant Patent Applications related to plants derived from the same breeding program. The Applications are entitled; *Campsis* Plant Named 'Takarazuka Zujin' (U.S. Plant patent application Ser. No. 13/385,116)* and *Campsis* Plant Named 'Takarazuka Fresa' (U.S. Plant patent application Ser. No. 13/385,122)*.

BACKGROUND OF THE INVENTION

The present invention relates to a new and distinct cultivar of *Campsis×tagliabuana* (*C. grandiflora×C. radicans*) and will be referred to hereafter by its cultivar name, 'Takarazuka Yellow'. 'Takarazuka Yellow' is a new cultivar of perennial vine for use as a landscape plant.

'Takarazuka Yellow' originated as a seedling that arose from seed planted from an open pollination of unnamed plants of *Campsis×tagliabuana* from the Inventor's breeding line in Shizuoka Prefecture Takarazuka, Japan in 1995. The parents are therefore unknown. The new *Campsis* was selected as a single unique plant in 2000.

Asexual reproduction of the new cultivar was first accomplished by the Inventor using softwood stem cuttings in 2008 in Takarazuka, Japan. The characteristics of the new cultivar have been determined to be stable and are reproduced true to type in successive generations.

SUMMARY OF THE INVENTION

The following traits have been repeatedly observed and represent the characteristics of the new cultivar as grown outdoors in trial beds and in containers in Takarazuka, Japan. These attributes in combination distinguish 'Takarazuka Yellow' as a unique cultivar *Campsis*.

1. 'Takarazuka Yellow' exhibits very dark green, clean foliage.

2. 'Takarazuka Yellow' exhibits large flowers that are peach orange in color when they open and mature to yellow in color, throats are orange-red with red veining.
3. 'Takarazuka Yellow' exhibits a compact, upright vining plant habit.

'Takarazuka Yellow' can be most closely compared to cultivars derived from the same breeding program; 'Takarazuka Fresa', 'Takarazuka Zujin' and 'Takarazuka Gold' (not patented). 'Takarazuka Fresa' differs from 'Takarazuka Yellow' in flowers that are red in color and smaller in size. 'Takarazuka Zijin' differs from 'Takarazuka Yellow' in having flowers that are coral red in color and in having a longer bloom season. 'Takarazuka Gold' differs from 'Takarazuka Yellow' in having flowers that are smaller, lighter and less orange in color, in having a less compact plant habit, and in having foliage that is lighter green. 'Takarazuka Yellow' can also be compared to the cultivar 'Kudian' (U. S. Plant Pat. No. 13,139). 'Kudian' differs from 'Takarazuka Yellow' in having flowers that are more orange in color with orange-red throats and in having pubescent leaves.

BRIEF DESCRIPTION OF THE DRAWING

The accompanying colored photograph illustrates the overall appearance and distinct characteristics of a one year-old plant of the new *Campsis* as grown outdoors in a one-gallon container in Takarazuka, Japan.

The photograph in FIG. 1 provides a view of a cluster of flowers of 'Takarazuka Yellow'.

Figure 1:
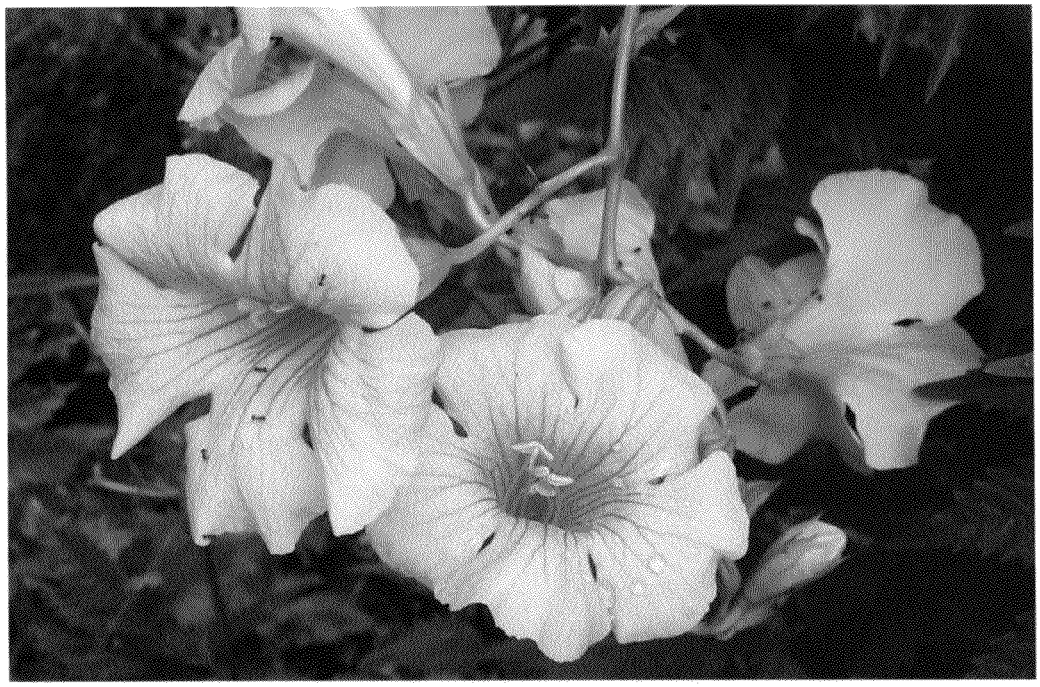
Figure 2:
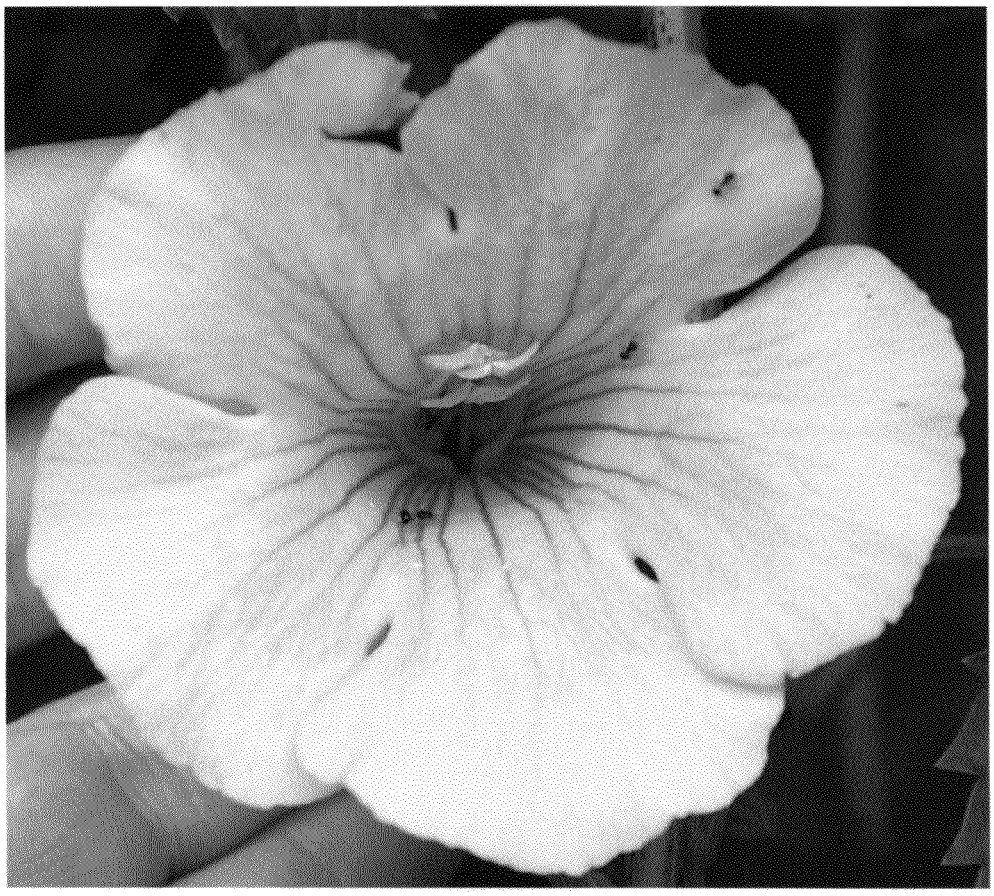

The photograph in FIG. 2 provides a close-up view of a flower of 'Takarazuka Yellow'.

The colors in the photographs are as close as possible with the digital photography techniques utilized and the color values cited in the detailed botanical description accurately describe the colors of the new *Campsis.*

DETAILED BOTANICAL DESCRIPTION

The following is a detailed description of one year-old plants of the new *Campsis* as grown outdoors in one-gallon containers in Takarazuka, Japan. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Blooms from May through July in Japan.

*Plant type.*—Perennial vine, deciduous in U.S.D.A. Zone 5.

*Plant habit.*—Compact, upright vine.

*Height and spread.*—Reaches about 40 to 50 cm in height and 50 cm width in one year.

*Hardiness.*—At least in U.S.D.A. Zone 5.

*Diseases resistance.*—No disease resistance or susceptibility has been observed.

*Root description.*—Fibrous.

*Propagation.*—Softwood stem cuttings.

*Growth rate.*—Vigorous.

*Root description.*—Fibrous.

Stem description:

*Shape.*—Round.

*Stem color.*—Young growth; 144B, mature wood 200D.

*Stem size.*—Main stems; 40 to 50 cm in length and an average of 2.6 mm in width, lateral branches; an average of 18 cm in length and 2 mm in width.

*Stem surface.*—Glabrous.

*Internode length.*—Average of 4.5 cm.

*Branching.*—5 lateral branches.

Foliage description:

*Leaf division.*—Pinnately compound with 7 to 13 leaflets.

*Leaf arrangement.*—Opposite.

*Leaf attachment.*—Petiolate.

*Leaf size.*—Range from 15 to 30 cm in length and 4 to 19 cm in width.

*Leaflet size.*—Range from 2 to 12 cm in length and 1 to 4.5 cm in width.

*Leaflet shape.*—Elliptic to ovate-oblong.

*Leaflet base.*—Cuneate.

*Leaflet apex.*—Acuminate to long acuminate.

*Leaflet venation.*—Pinnate, not prominent, color on upper surface 144A to 144B on upper and lower surface.

*Leaflet margins.*—Irregularly serrated to crenated.

*Leaflet arrangement.*—Odd pinnate.

*Leaflet attachment.*—Winged petiolules.

*Leaflet aspect.*—Slightly concave from midrib.

*Leaflet surface.*—Glabrous, smooth and moderately glossy on upper surface and glabrous, smooth and slightly glossy on lower surface.

*Leaflet color.*—New growth upper surface and lower surface; 144A, mature leaves upper surface; 137A, mature leaves lower surface; 137B.

*Petioles.*—Range from 4 to 7 cm and an average of 2.5 mm in length, 137A in color, very sparsely pubescent surface.

*Petiolules.*—Ranges from 0.5 cm and 1 cm in length and an average of 2 mm in width, winged with base swollen, 137B in color, glabrous surface.

*Rachis.*—Ranges from 7 to 11 cm in length (including petiole) and an average of 2 mm in width, 137B in color, sparsely pubescent surface.

*Stipules.*—Not present.

Inflorescence description:

*Inflorescence type.*—Terminal cluster of single flowers, blooms on current year's growth.

*Inflorescence size.*—An average of 26 cm in depth and width.

*Flower buds.*—Elliptic in shape, about 2 cm in length and 1.5 cm in width, color is 40A suffused with 42A.

*Flower fragrance.*—None noted.

*Lastingness of flowers.*—Individual flowers last about 5 to 7 days.

*Flower quantity.*—5 to 12 flowers per inflorescence.

*Flower type.*—Tubular.

*Flower aspect.*—Upright to outward.

*Flower size.*—9 to 10 cm in length, 9 cm in diameter at apex and 5 mm in diameter at base.

*Peduncles.*—Average of 8 cm in length and 3 mm in diameter, 144B in color, glabrous surface, round in shape, held upright to about a 30° angle to stem (0% is vertical).

*Pedicels.*—Average of 3.5 cm in length and 1.5 mm in diameter, round in shape, 144A in color, glabrous surface.

*Calyx form.*—Campanulate with base fused.

*Sepals.*—5, lanceolate in shape, apiculate apex, fused base, an average of 2.5 cm in length and 6 mm in width, entire margin, color of upper and lower surface is a blend of 144A, 144B and 144C, glabrous and satiny surface.

*Corolla.*—Tubular with apex flared, tube is an average of 6.5 cm in length and 1.4 cm in width.

*Petals.*—5, flabellate in shape with lobes rounded, upper and lower surface is smooth, margin entire to slightly notched and wavy, fused base, round apex, about 9 cm in length with lobe portion about 4 cm in width and depth, color of upper and lower surface when opening: 22A and becoming 23D, color of upper and lower surface when mature; 11C and shaded with 23D, throat on inner surfaces young and mature; a blend of 32A and 23C with veins of 32A, color of outer surface of tube portion same as lobe coloration.

Reproductive organs:

*Gynoecium.*—Pistil; 1, about 5.5 mm in length, 26D in color.

*Androcoecium.*—Stamens; 4, anthers; narrowly elliptic in shape, an average of 3 cm in length, 18Din color, pollen; moderate in quantity and 11D in color.

*Seed.*—Not observed.

It is claimed:

1. A new and distinct cultivar of *Campsis* plant named 'Takarazuka Yellow' as herein illustrated and described.

* * * * *